United States Patent
Suzuki et al.

(10) Patent No.: US 8,941,081 B2
(45) Date of Patent: Jan. 27, 2015

(54) MICROPARTICLE MEASUREMENT APPARATUS AND MICROPARTICLE ANALYSIS METHOD

(71) Applicant: Sony Corporation, Tokyo (JP)

(72) Inventors: Shunpei Suzuki, Chiba (JP); Gakuji Hashimoto, Kanagawa (JP)

(73) Assignee: Sony Corporation (JP)

(*) Notice: Subject to any disclaimer, the term of this patent is extended or adjusted under 35 U.S.C. 154(b) by 0 days.

(21) Appl. No.: 13/939,920

(22) Filed: Jul. 11, 2013

(65) Prior Publication Data

US 2014/0021370 A1 Jan. 23, 2014

(30) Foreign Application Priority Data

Jul. 18, 2012 (JP) ................. 2012/159754

(51) Int. Cl.
| | | |
|---|---|---|
| *G01J 1/58* | (2006.01) | |
| *H01L 27/00* | (2006.01) | |
| *G01N 15/02* | (2006.01) | |
| *G01N 21/00* | (2006.01) | |
| *G01N 21/64* | (2006.01) | |
| *G01N 15/14* | (2006.01) | |
| *G01N 15/10* | (2006.01) | |

(52) U.S. Cl.
CPC ........ G01N 21/6486 (2013.01); G01N 15/1459 (2013.01); *G01N 2015/1006* (2013.01); *G01N 2015/149* (2013.01)
USPC ........ 250/459.1; 356/335; 356/336; 356/337; 356/433; 250/458.1; 250/208.1

(58) Field of Classification Search
CPC ............ G01N 21/6486; G01N 15/147; G01N 21/645; G01N 21/6428
USPC ..................... 356/335–443, 73, 39
See application file for complete search history.

(56) References Cited

U.S. PATENT DOCUMENTS

| | | | | |
|---|---|---|---|---|
| 8,466,435 | B2 * | 6/2013 | Toishi et al. ............... | 250/458.1 |
| 8,780,338 | B2 * | 7/2014 | Suzuki et al. ................... | 356/73 |
| 2011/0269175 | A1 * | 11/2011 | Durack et al. .................. | 435/29 |
| 2013/0037726 | A1 * | 2/2013 | Kiesel et al. ............... | 250/458.1 |

FOREIGN PATENT DOCUMENTS

JP 2010-190680 A 9/2010

* cited by examiner

*Primary Examiner* — Tarifur Chowdhury
*Assistant Examiner* — Sunghee Y Gray
(74) *Attorney, Agent, or Firm* — Sheridan Ross P.C.

(57) ABSTRACT

There is provided a microparticle measurement apparatus including a first light source configured to irradiate excitation light on a droplet containing a microparticle, the droplet being discharged from an orifice, a second light source configured to irradiate illumination light on the droplet for acquiring an image of the droplet, a light receiving element configured to detect fluorescence generated from the microparticle due to the irradiation of the excitation light, and to acquire an image of the droplet, and a filter member configured to be arranged between the droplet and the light receiving element. The filter member includes a first area through which the fluorescence and the illumination light pass, and a second area that is provided around the first area and that has a wavelength selectivity which lets the fluorescence pass through but blocks the illumination light.

8 Claims, 6 Drawing Sheets

MICROPARTICLE MEASUREMENT APPARATUS AND MICROPARTICLE ANALYSIS METHOD

BACKGROUND

The present technology relates to a microparticle measurement apparatus and a microparticle analysis method. More specifically, the present technology relates to a microparticle measurement apparatus and the like for ensuring both a sufficient fluorescence intensity from droplets discharged from an orifice and a sufficient depth of field of a droplet image.

A microparticle measurement apparatus that optically, electrically, or magnetically detects the properties of microparticles in a cell, for example, and separates and recovers only the microparticles having a predetermined property (e.g., a flow cytometer) is known.

In cell separation performed in a flow cytometer, first, a fluid stream (a laminar flow of a sample solution including cells and a sheath fluid) from an orifice formed in a flow cell is generated, the fluid stream is turned into droplets by applying vibrations on the orifice, and a charge is applied on the droplets. Further, the movement direction of the cell-containing droplets discharged from the orifice is electrically controlled in order to recover a target cell having a desired property and the other non-target cells in separate recovery vessels.

For example, as a microchip type flow cytometer, JP-A-2010-190680 discloses a "micro-particle sorting apparatus including a microchip in which a flow path through which liquid containing a microparticle flows and an orifice through which the liquid flowing through the flow path is discharged into a space outside the chip, an oscillating element configured to transform the liquid into liquid droplets and discharge the liquid droplets at the orifice, a charge mechanism for adding an electric charge to the discharged liquid droplets, an optical detection mechanism that detects an optical property of the microparticles flowing through the flow path, paired electrodes provided so as to be opposed to each other while sandwiching the moving liquid droplets therebetween along a movement direction of the liquid droplets discharged into a space outside the chip, and two or more containers that collect the liquid droplets passing between the paired electrodes".

On the other hand, with a flow cytometer, in the illumination system, optical axis correction (calibration) for adjusting the laser light so that it is at right angles to the sample flow and is in focus is performed in order to efficiently detect scattered light and fluorescence generated from the microparticles. This calibration is performed by flowing microbeads for calibration (hereinafter, also referred to as "calibration beads"), adjusting the position and focus of a condenser lens while watching histogram data about those calibration beads, and centering the light source so that the positional relationship of the laser light, the sample flow, and the detector is optimized

SUMMARY

Due to differences in individual microchips, the ejection angle of the fluid stream ejected from a microchip is different for each microchip. This means that the fluid stream deviates in the depth direction of the observation optical system. If the fluid stream greatly deviates, the fluid stream image (or droplet image) becomes blurry. Thus, in practice, the user visually confirms deviation in the fluid stream, and performs a manual adjustment if deviation has occurred.

If sorting system calibration is performed based on information about the droplet image, it is desirable to have little droplet image blur, and to acquire as many fluorescence signals from the calibration beads as possible. However, to ensure a sufficient level of fluorescence signal from the calibration beads, the aperture number (NA) of the optical system has to be set high. Further, if the aperture number (NA) is set high, this results in a decrease in the field of depth.

According to an embodiment of the present disclosure, there is provided a microparticle measurement apparatus capable of simultaneously obtaining a sufficient depth of field of a droplet image and a sufficient fluorescence intensity.

According to an embodiment of the present technology, there is provided a microparticle measurement apparatus including a first light source configured to irradiate excitation light on a droplet containing a microparticle, the droplet being discharged from an orifice, a second light source configured to irradiate illumination light on the droplet for acquiring an image of the droplet, a light receiving element configured to detect fluorescence generated from the microparticle due to the irradiation of the excitation light, and to acquire an image of the droplet, and a filter member configured to be arranged between the droplet and the light receiving element. The filter member includes a first area through which the fluorescence and the illumination light pass, and a second area that is provided around the first area and that has a wavelength selectivity which lets the fluorescence pass through but blocks the illumination light.

In this microparticle measurement apparatus, by providing a filter member having a first area through which the fluorescence and the illumination light pass, and a second area that lets the fluorescence pass through but blocks the illumination light between the droplet and the light receiving element, fluorescence is acquired at a high numerical aperture (NA), and the droplet image is acquired at a low numerical aperture (NA).

The first area may be preferably provided at a center portion of the filter member, and the second area is provided at a peripheral portion of the filter member.

Further, the first area may be preferably a through hole provided in the filter member, and the first area may be preferably formed from a transparent member.

Meanwhile, the second area may be preferably formed from a short-pass filter.

The second light source may preferably emit the illumination light having a longer wavelength than the fluorescence. For example, the second light source may be preferably an LED.

Further, according to an embodiment of the present technology, there is provided a microparticle analysis method including irradiating excitation light on a droplet containing a microparticle and detecting, with a light receiving element, fluorescence generated from the droplet irradiated with the excitation light that has passed through a first area and a second area of a filter member, the droplet being discharged from an orifice, and irradiating illumination light on the droplet and acquiring a droplet image with the light receiving element by blocking the illumination light irradiated on the droplet at the second area of the filter member and letting the illumination light pass through only the first area.

In an embodiment of the present technology, the term "microparticle" has a broad meaning that includes biologically-relevant microparticles such as cells, microbes, ribosomes and the like, as well as synthetic particles such as latex particles, gel particles, industrial particles and the like.

Examples of biologically-relevant microparticles include the chromosomes, liposomes, mitochondria, organelles (cell organelles) that form various cells. Examples of cells include animal cells (hematopoietic cells etc.) and plant cells.

Examples of microbes include bacteria such as *E. coli*, viruses such as tobacco mosaic virus, fungi such as yeast and the like. Further example of biologically-relevant microparticles includes nucleic acids, proteins, complexes of these and the like. Examples of industrial particles include organic or inorganic polymer materials, metals and the like. Examples of organic polymer materials include polystyrene, styrene-divinyl benzene, poly methyl methacrylate and the like. Examples of inorganic polymer materials include glass, silica, magnetic materials and the like. Examples of metals include metal colloids, aluminum and the like. Although the shape of these microparticles is usually spherical, the microparticles may also have a non-spherical shape. Further, the size and mass of these microparticles is not especially limited.

According to the embodiments of the present disclosure described above, there is provided a microparticle measurement apparatus capable of simultaneously obtaining a sufficient depth of field of a droplet image and a sufficient fluorescence intensity.

DETAILED DESCRIPTION OF THE EMBODIMENT(S)

Figure 1:
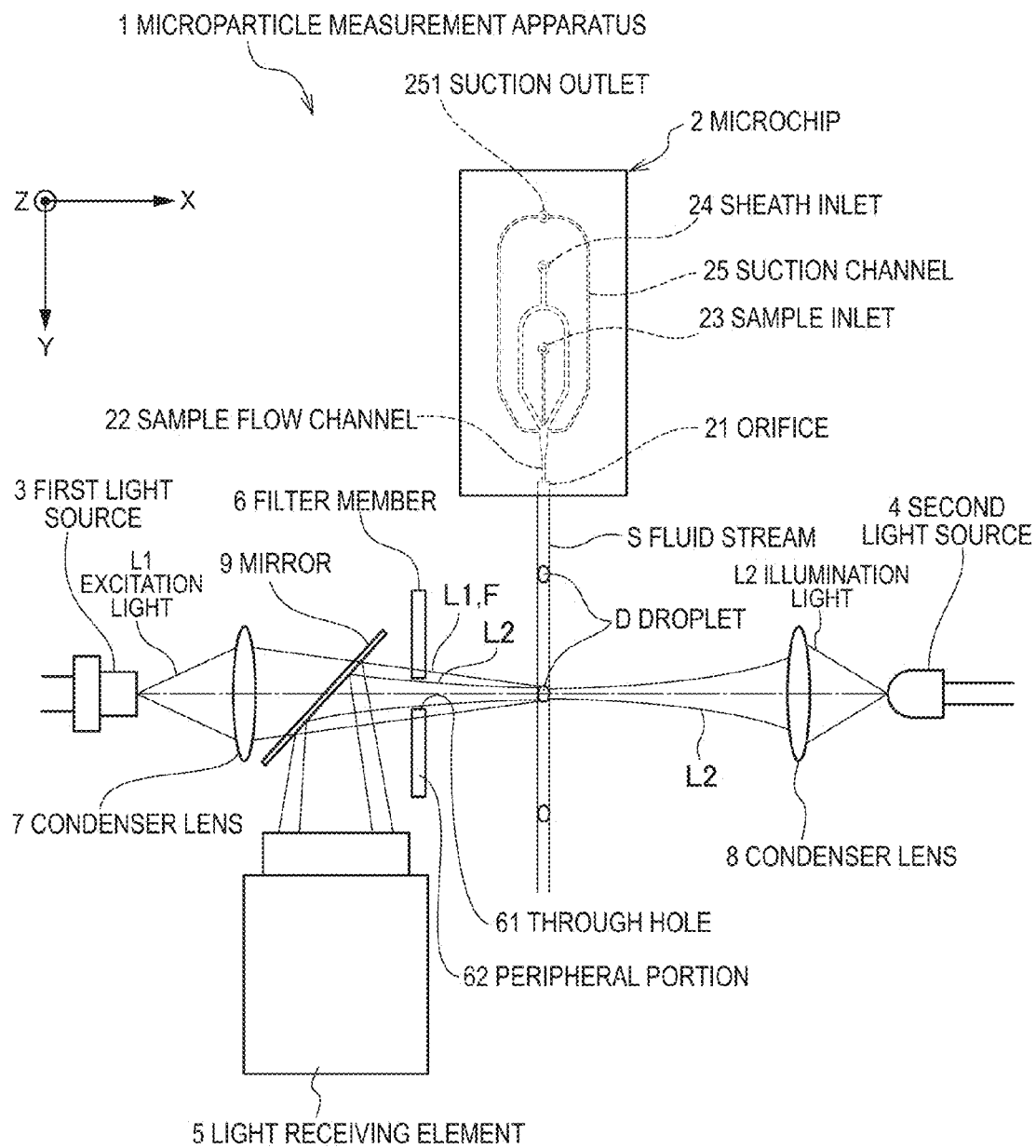
FIG. 1 is a schematic diagram illustrating an optical system for calibration during sorting performed by a microparticle measurement apparatus according to an embodiment of the present technology.

Hereinafter, preferred embodiments of the present disclosure will be described in detail with reference to the appended drawings. Note that, in this specification and the appended drawings, structural elements that have substantially the same function and structure are denoted with the same reference numerals, and repeated explanation of these structural elements is omitted. The description will be made in the following order.
1. Microparticle measurement apparatus configuration
(1) Microchip
(2) First light source (fluorescence detection system)
(3) Second light source (imaging system)
(4) Filter member
(5) Light receiving element
(6) Sorting system
(7) Control unit etc.

2. Operation of the microparticle measurement apparatus

1. Microparticle Measurement Apparatus

FIG. 1 is a schematic diagram illustrating an optical system for calibration during sorting performed by a microparticle measurement apparatus 1 (hereinafter also referred to as "flow cytometer 1") according to an embodiment of the present technology that is configured as a microchip type flow cytometer.

In the flow cytometer 1 illustrated in FIG. 1, a channel system is configured from a microchip 2 capable of disposable use. With this microchip 2, cross-communication of the sample during the measurement period can be prevented.

The flow cytometer 1 includes a first light source 3 that irradiates excitation light L1 on a microparticle-containing droplet D discharged from an orifice 21 of the microchip 2, and a second light source 4 that irradiates illumination light L2 on the droplet D to acquire an image of the droplet D.

Further, the flow cytometer 1 includes a light receiving element 5 that detects fluorescence F generated from the microparticles (or from a fluorescence substance labeled on the microparticles) irradiated with the excitation light L1 and acquires a droplet image, and a filter member 6 arranged between the droplet D and the light receiving element 5.

First, the microchip 2 including the orifice 21 that discharges the microparticle-containing droplet D will be described, and then the optical system (the fluorescence detection system and the imaging system) for calibration during sorting performed by the flow cytometer 1 will be described.

(1) Microchip

On the microchip 2, channels (sample channel 22 etc.) are formed into which a sample solution including target microparticles that are the measurement target or a calibration liquid including reference microparticles (calibration beads) is introduced. The term calibration beads refers to microparticles for calibration that have been prepared so as to exhibit uniform optical characteristics.

The term "sample solution" mentioned below includes both the sample solution and the calibration solution. Further, the term "microparticles" mentioned below includes both the detection target microparticles and calibration beads.

The microchip 2 is configured from a substrate on which channels (sample channel 22 etc.) are formed. The substrate is formed from glass or various resin materials, such as PC, PMMA, PE, PP, PS, polydimethysiloxane (PDMS) and the like.

The formation of the channels on the substrate can be carried out by, for example, wet or dry etching of a glass substrate, injection molding of a thermoplastic resin material, nano-imprinting or machining of a resin substrate and the like. Further, the microchip 2 can also be formed by sealing the substrate on which the channels are formed with a substrate of the same or a different material.

The channels on the microchip 2 are configured so that a three-dimensional laminar flow is formed, in which a sample solution laminar flow is positioned in the center of a sheath fluid laminar flow. In the microchip 2 illustrated in FIG. 1, the sample solution is introduced into a sample inlet 23 from a feed connector, merges with a sheath fluid introduced from a feed connector into a sheath inlet 24, and is fed to a sample flow channel 22. The sheath fluid introduced from the sheath inlet 24 is split and fed in two directions, and then merges with the sample solution introduced from the sample inlet 23 so as to sandwich the sample solution from two directions. Consequently, a three-dimensional laminar flow is formed, in which a sample solution laminar flow is positioned in the center of a sheath fluid laminar flow.

A suction channel 25 may also be formed for getting rid of blockages or air bubbles that can form in the sample flow channel 22 by applying a negative pressure in the sample flow channel 22 to temporarily reverse the flow. A suction outlet 251 connected via the feed connector to a negative pressure source, such as a vacuum pump, is formed on one end of the suction channel 25. The other end of the suction channel is connected to the sample flow channel 22.

Further, the flow cytometer 1 can be configured so that the detection of the cell properties is carried out in the sample flow channel 22. For example, for optical detection, laser light is irradiated on cells that are arranged and fed in a line in the center of the three-dimensional laminar flow through the sample flow channel 22, and the scattered light and fluorescence generated from the cells are detected by a (not illustrated) light detector.

The orifice 21 is provided at one end of the sample flow channel 22 formed on the microchip 2. From the orifice 21, the three-dimensional laminar flow becomes a fluid stream S, and is discharged. In FIG. 1, the discharge direction of the fluid stream from the orifice 21 is indicated by the positive direction of the Y axis. The fluid stream S ejected from the orifice 21 is turned into droplets by vibrations applied on the whole of the microchip 2 or on the orifice 21 by a chip vibrator unit, such as a piezo vibration element.

2) First Light Source (Fluorescence Detection System

The first light source 3 is a light source capable of emitting excitation light L1. As the first light source 3, it is preferred to use a laser diode (hereinafter referred to as "LD"). Other examples that can be used as the first light source 3 include a SHG (second harmonic generation) laser, a solid laser, a gas laser, a high luminance LED (light-emitting diode) and the like.

The laser light (excitation light) L1 emitted from the first light source (LD) 3 is focused by a condenser lens 7, passes through a mirror and a filter member 6, and is irradiated on the droplet D in the fluid stream S that is ejected from the orifice 21.

Fluorescence and scattered light from the microparticles or from a fluorescent substance labeled on the microparticles are emitted by the laser light (excitation light) L1 irradiated on the droplet D. Here, the fluorescence and the scattered light components (e.g., backward scattered light and side scattered light etc.) are important light components for obtaining the properties of the microparticles.

Fluorescence F emitted from the microparticles and the like due to the irradiation of the laser light L1 from the LD 3 passes through the filter member 6, is reflected by the mirror 9, and is detected by the light receiving element 5. As the mirror 9, a dynamic mirror that lets the excitation light L1 to pass through but reflects the fluorescence F can be used.

3) Second Light Source (Imaging System

The second light source 4 irradiates light for illumination (illumination light) L2 on the microparticle-containing droplet D in the fluid stream S in order to acquire an image of the droplet D. In FIG. 1, an example is illustrated in which the illumination light L2 emitted from the second light source 4 is focused by a condenser lens 8 on the microparticle-containing droplet D in the fluid stream S.

It is preferred to use as the second light source 4 a light-emitting diode (hereinafter referred to as "LED") 4, as compared with an LD, an LED is more capable of uniformly irradiating the microparticle-containing droplet D, is less expensive, and has a longer life. Further, also from the perspective that a short-pass filter can be used for the below-described filter member 6, it is preferred to use an LED 4 that can emit illumination light that has a longer wavelength than the fluorescence.

Conventionally, although an LD has often been used for the illumination light too, since it is difficult to uniformly irradiate the droplet D with laser light, it was difficult to acquire a clear droplet image. However, using the LED 4 for the illumination light enables a clear droplet image to be acquired by uniformly irradiating the microparticle-containing droplet D.

Further, since LEDs are commercially available in various wavelengths, using an LED as the second light source 4 allows a broader selection of choices for the illumination light L2 wavelength. In an embodiment of the present technology, it is preferred to use an LED 4 that emits illumination light with a wavelength close to the fluorescence F.

In the imaging system according to an embodiment of the present technology, the acquisition of the fluorescence from the microparticles and the acquisition of the droplet image are performed by a common optical system (one light receiving element 5). Consequently, if the difference between the wavelength of the fluorescence F and the wavelength of the illumination light L2 is large, due to chromatic aberration, either one of the fluorescence image or the droplet image may be blurry. However, generally, since there is a wider selection of choices for LEDs than LDs, by selecting an LED 4 that emits illumination light L2 with a wavelength close to the fluorescence F, such a problem can be avoided.

The illumination light L2 emitted from the second light source (LED) 4 is irradiated on the microparticle-containing droplet D, and a droplet image is captured by the light receiving element 5. During this process, since the illumination light L2 passes through only a through hole 61 of the filter member 6, and is blocked by a peripheral portion 62, which is the remaining portion excluding the through hole 61, a deep depth of field can be obtained. Next, the configuration of the filter member 6 will be described in detail.

Filter Member

The filter member 6 is arranged on an optical path between the fluid stream S (or the droplet D) that is ejected from the orifice 21 of the microchip 2 and the light receiving element 5.

Figure 2:
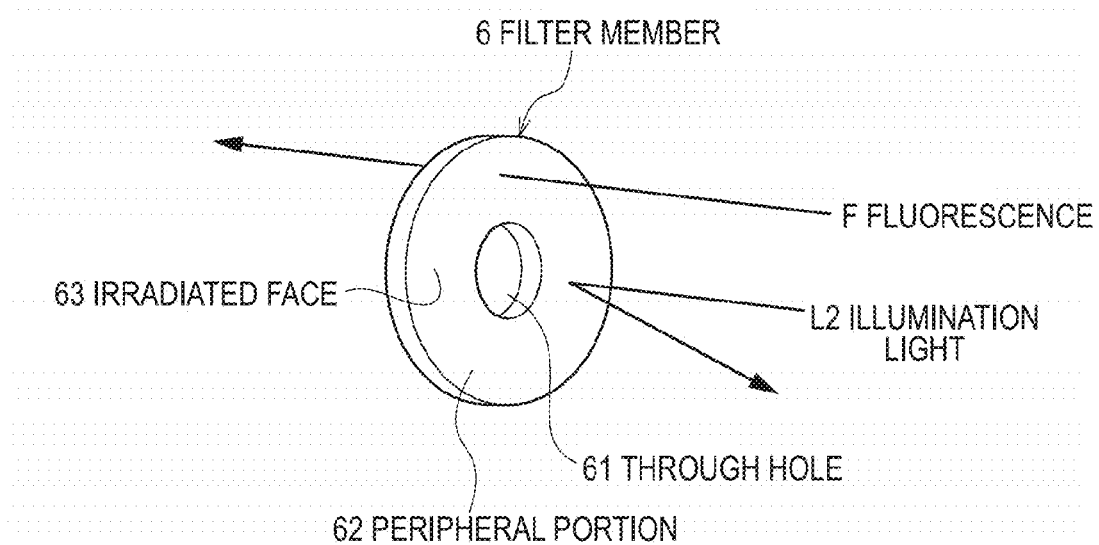
FIG. 2 is a schematic diagram illustrating a configuration of an example of a filter member used in a microparticle measurement apparatus according to an embodiment of the present technology.

This filter member 6 is configured from an optical filter having a wavelength selectivity that lets the laser light (excitation light) L1 emitted from the first light source (LD) 3 and the fluorescence F generated from the microparticles to pass through, but blocks the illumination light L2 emitted from the second light source (LED) 4. Further, as illustrated in FIG. 2, the optical filter (filter member 6) is provided with a through hole 61.

The site of the through hole 61 in the filter member 6 is at an area (hereinafter referred to as "first area") through which the excitation light L1, the illumination light L2, and the fluorescence F passes. The peripheral portion 62 around the through hole 61 (first area) is an area (hereinafter referred to as "second area") that, due to the nature of the wavelengthselective optical filter, lets the excitation light L1 and the fluorescence F pass through, but blocks the illumination light L2.

Since it is desirable for the optical system according to an embodiment of the present technology to have rotational symmetry, it is preferred to provide the first area (through hole) 61 in a center portion, and the second area (peripheral portion) 62 at a site of the remaining portion (a site around the through hole 61) excluding the center portion 61.

Although the relative size (surface area) of each of the first area 61 and the second area 62 with respect to the filter member 6 is not especially limited, it is desirable to determine the respective surface areas based on a balance between image sharpness (MTF) and depth of field.

Generally, since the excitation light L1 has a shorter wavelength then the fluorescence F, it is preferred to use an LED 4 that emits illumination light L2 having a longer wavelength than the fluorescence wavelength, and a short-pass filter as the optical filter. With a filter member 6 that is configured from a short-pass filter, the excitation light L1 and the fluorescence F can pass through the through hole (center portion) 61 and the peripheral portion 62 of the filter member 6, and the illumination light L2 can be blocked by the peripheral portion 62. Further, based on the wavelength of the illumination light L2 of the second light source 4, a long-pass filter, a band-pass filter and the like can also be used as the optical filter.

Figure 3:
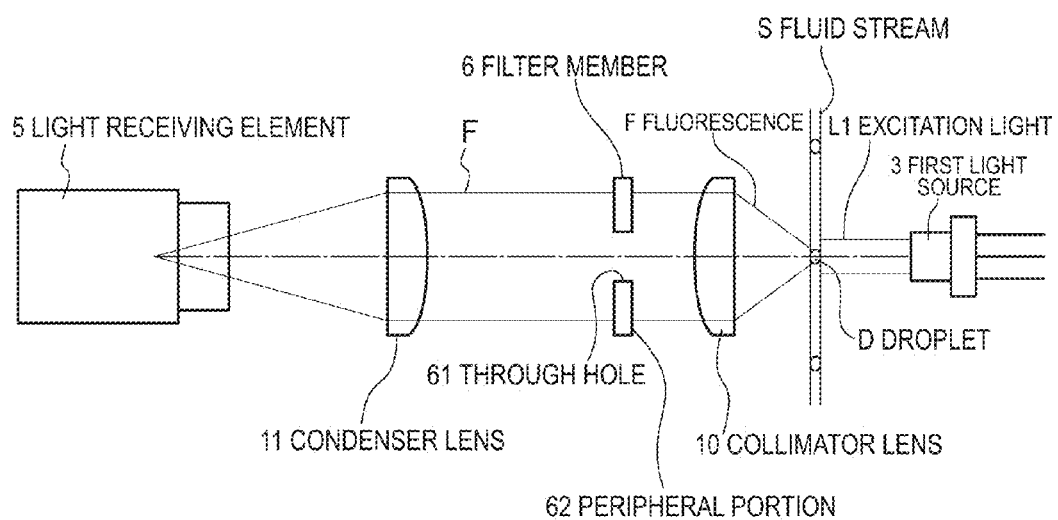
FIG. 3 is a schematic diagram illustrating an example of an optical system for detecting fluorescence generated from microparticles irradiated with excitation light by a microparticle measurement apparatus according to an embodiment of the present technology.
Figure 4:
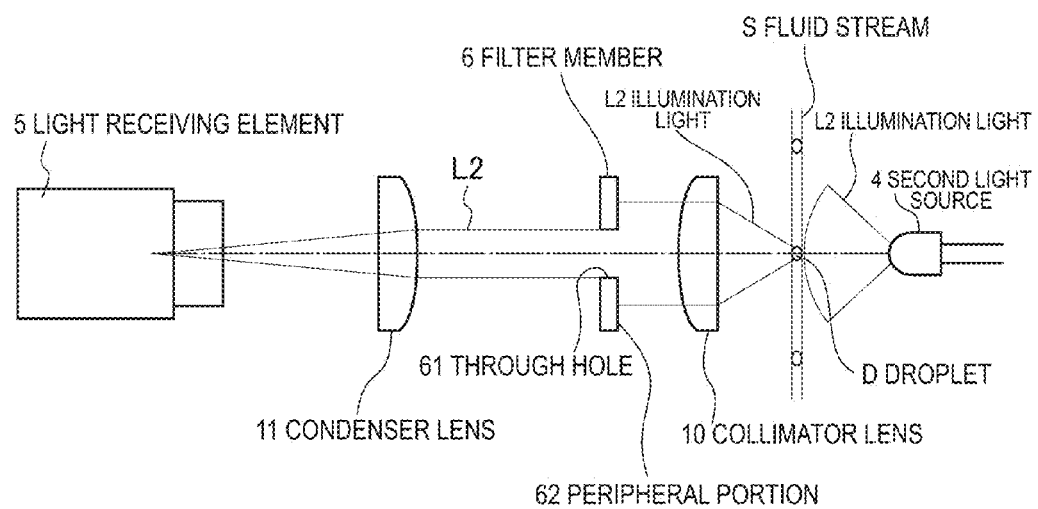
FIG. 4 is a schematic diagram illustrating an example of an optical system for capturing an image of a droplet irradiated with illumination light by a microparticle measurement apparatus according to an embodiment of the present technology.

Next, for ease of description, the difference between the numerical aperture (NA) of the first light source (LD) 3 and the second light source (LED) 4 will be described based on respectively separate optical systems with reference to FIGS. 3 and 4. FIG. 3 is a schematic diagram illustrating an example of an optical system for detecting fluorescence generated from microparticles irradiated with excitation light. FIG. 4 is a schematic diagram illustrating an example of an optical system for capturing an image of a droplet irradiated with illumination light.

It is noted that the optical systems illustrated in FIGS. 3 and 4 are configured by arranging a collimator lens 10 between the droplet D (or the fluid stream S) and the filter member 6, and arranging a condenser lens 11 between the filter member 6 and the light receiving element 5.

As illustrated in FIG. 3, the excitation light L1 emitted from the first light source (LD) 3 is irradiated on the microparticles in the droplet D, and the fluorescence F emitted from the excited microparticles passes through the whole of the irradiated face of the filter member 6. Consequently, the fluorescence F can be acquired by the light receiving element 5 at a high NA, and measured at a high sensitivity even for faint fluorescence F.

On the other hand, as illustrated in FIG. 4, the illumination light L2 emitted from the second light source (LED) 4 passes through only the through hole (first area) 61 of the filter member, and is blocked by the peripheral portion 62 that excludes the through hole 61 of the filter member 6. Consequently, the illumination light L2 can be acquired by the light receiving element 5 at a low NA, so that the depth of field of the droplet image can be deeper.

Thus, in an embodiment of the present technology, a sufficient fluorescence intensity of the microparticles included in the droplet D and a sufficient depth of field of the droplet image can be simultaneously obtained by the filter member 6 arranged on the optical path between the droplet D and the light receiving element 5.

It is noted that deviation in the ejection angle (refer to θ in FIG. 5) of the fluid stream S ejected from the orifice 21 can occur even in the Z axis direction of FIG. 1. However, with the optical system according to an embodiment of the present technology, as described above, since the effective NA can be switched based on the objective, the fluorescence signal is brighter (fluorescence intensity is higher) and the bright field image can be acquired more clearly (focal depth is deeper) even for deviation in the Z axis direction of the fluid stream S.

Figure 5:
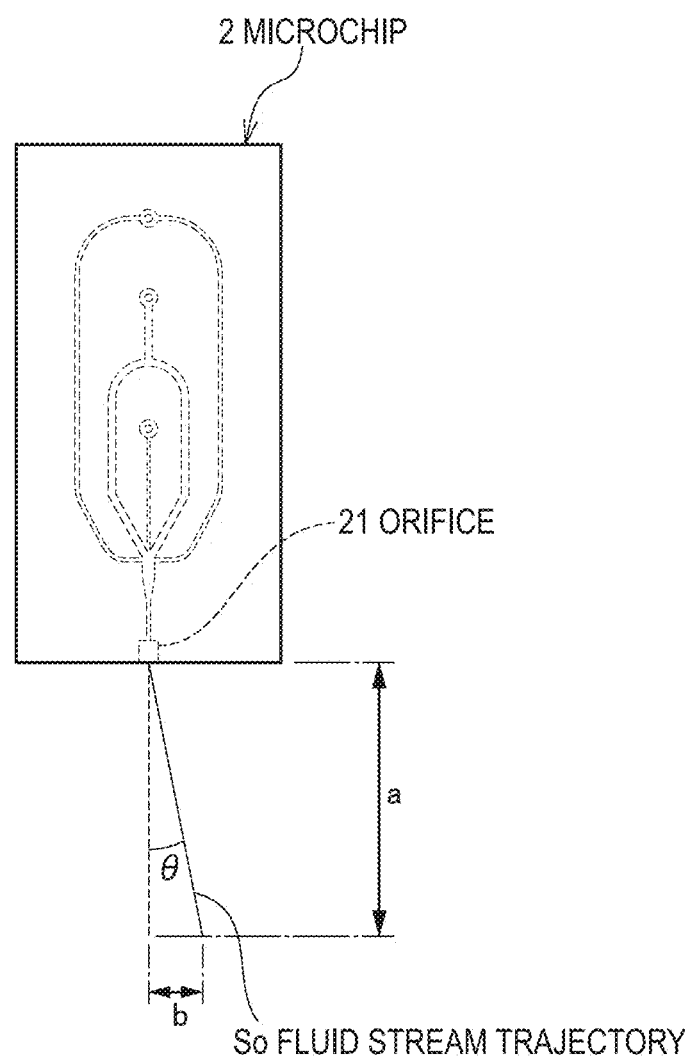
FIG. 5 is a schematic diagram illustrating unevenness in the trajectory of a fluid stream ejected from an orifice in a microchip, which shows the diameter of a through hole provided in a filter member.
Figure 6:
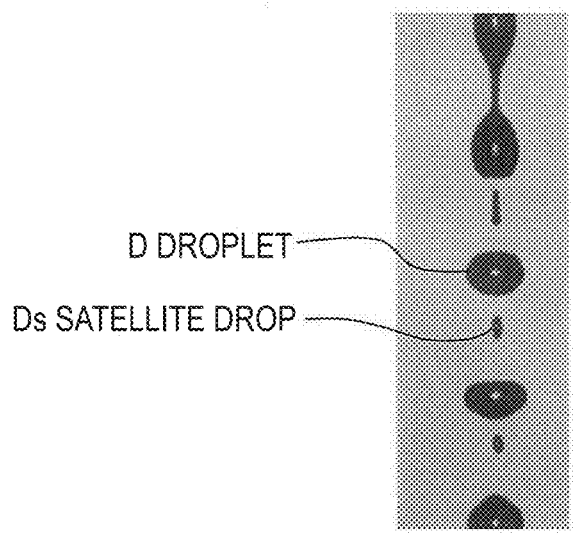
FIG. 6 illustrates an example of a droplet image captured by a light receiving element in a microparticle measurement apparatus.

Next, the diameter of the through hole 61 provided in the filter member 6 will be described with reference to FIGS. 5 and 6. FIG. 5 is a schematic diagram illustrating unevenness in the trajectory of the fluid stream S ejected from the orifice 21 of the microchip 2. FIG. 6 illustrates an example of a droplet image captured by the light receiving element 5 from a droplet D discharged from the orifice 21 of the microchip 2.

As illustrated in FIG. 5, due to differences in individual microchips 2, the trajectory So of the fluid stream ejected from the orifice 21 is slightly different, so that the fluid stream can be ejected having variation from the angle θ (for example, about 0°±1 (e.g., about ±0.5°)) with respect to the perpendicular direction.

Based on this angle θ and a distance a (for example, about 0 to 20 mm (e.g., about 16 mm))) until the position (break off point) where the droplet starts to be formed from an end of the microchip 2 (aperture edge of the 21), a trajectory displacement b of the fluid stream at an observation site of the droplet is approximately a×tan θ (e.g., about ±0.14 mm) This is set as the depth of field specification of the observation optical system.

On the other hand, as illustrated in FIG. 6, when the droplet D is formed from the fluid stream S discharged from the orifice 21, a satellite drop Ds that is smaller than the droplet D (e.g., having a diameter of about 20 μm) is observed.

Since droplet formation is performed by confirming and managing the shape of this satellite drop Ds, the ability to image the satellite drop Ds is a precondition. The diameter of the through hole 61 of the filter member 6 is a value (e.g., about 2 mm) designed so as to satisfy the above-described two conditions of depth of field and imaging resolution.

It is noted that it is sufficient for the filter member 6 to include the first area 61 through which the illumination light L2 and the fluorescence F pass through and the second area 62, which has wavelength selectivity such that the fluorescence F passes through but the illumination light L2 is blocked. Further, as the filter member 6, a filter member having a different configuration to that described above (refer to FIG. 2), in which the through hole 61 is provided in an optical filter, may also be used.

For example, the filter member may also be configured so that the first area is formed from a transparent member, and the second area is formed from an optical filter having wavelength selectivity, such as a short-pass filter. In this case, for example, transparent glass or a transparent resin, such as PMMA or PC, can be used for the transparent member.

Further, the filter member 6 may also be, for example, a filter member in which the first area and the second area are configured from optical filters having wavelength selectivity that are different to each other.

As the filter member, it is preferred to employ the above-described configuration in which the through hole 61 is provided in an optical filter (refer to FIG. 2), as this allows production to be carried out cheaply and easily.

The shape and the thickness of the filter member 6 are not especially limited. For example, the shape may be round, elliptical, square, polygonal and the like. The thickness may be around 0.5 to 10 mm. The shape of the first area (through hole) 61 may match the shape of the filter member, or may be a different shape to the filter member.

(5) Light Receiving Element

The light receiving element 5 functions as a "fluorescence detection unit" that detects the fluorescence F that is emitted from the microparticles or a fluorescent substance labeled on the microparticles, and also as a "droplet camera" that acquires a droplet image when the illumination light L2 is irradiated from the second light source 4 on the droplet D.

The light receiving element 5 captures an image of the fluid stream S that is ejected from the orifice 21 of the microchip 2 or of the droplet D discharged from the orifice 21. As the light receiving element 5, it is preferred to use a CCD camera, a CMOS image sensor and the like.

The image captured by the light receiving element 5 is displayed on a display unit such as a display, and is utilized by the user to confirm the formation state (droplet size, shape, interval etc.) of the droplets at the orifice 21. Further, the captured droplet image is also subjected to image processing in order to be utilized for formation of the droplets into a desired shape.

Further, in the flow cytometer 1, the trajectory of the fluid stream S (or the droplet D) ejected from the orifice 21 is different due to differences in the individual microchip 2 that is mounted, so that the position of the fluid stream S can change in the Z axis direction (or in the X axis direction) each time the microchip 2 is replaced. The light receiving element 5 can also be utilized to detect such positional changes in the Z axis direction (and in the X axis direction) of the fluid stream S.

In addition, in the flow cytometer 1, it may be desirable to change the droplet formation parameters (sheath pressure, droplet frequency, piezo drive voltage etc.) when the microchip 2 is replaced with a new chip or the external environment (temperature etc.) changes. In such a case, the time from when the microparticles are detected by a light irradiation detection unit until a charge is applied on the microparticle-containing droplets (hereinafter, this time is also referred to as "delay time") can be adjusted. The fluorescence acquired by the optical system according to an embodiment of the present technology can be utilized in order to determine this delay time.

(6) Sorting System

The configuration for sorting the microparticles in the fluid stream S ejected from the orifice 21 can be configured in the same manner as a conventional microparticle measurement apparatus (including a microparticle sorting apparatus and a cell sorter). Specifically, the sorting configuration can include a charge unit that applies a charge to the microparticle-containing droplet D discharged from the orifice 21, a pair of opposing deflection plates that are arranged along a movement direction of the droplet D discharged from the orifice 21 and that sandwich the droplet D, and a plurality of recovery vessels for receiving the microparticle-containing droplet D.

The pair of deflection plates include an electrode that controls the movement direction of the droplet D with an electrical force acting on the charge applied on the droplets by the charge unit. Further, the deflection plates also control the trajectory of the fluid stream S ejected from the orifice with an electrical force acting on the charge applied on the fluid stream S. The droplet D discharged from the orifice 21 is guided to and recovered in an arbitrary one of the plurality of vessels based on the presence or magnitude of an electrical force acting between the deflection plates.

(7) Control Unit Etc

The flow cytometer 1 includes, in addition to the above-described configuration, parts that a normal flow cytometer has, such as a light irradiation detection unit for detecting the optical properties of cells, a data analysis unit for determining properties, tank portions for storing the sample solution and the sheath fluid, a control unit for controlling each of the above-described parts and the like.

The control unit can be configured from a versatile computer including a memory, a hard disk and the like. The hard disk stores, for example, an OS and a program for executing the below-described microparticle analysis method.

Further, the light irradiation detection unit is configured from an irradiation system formed from an LD, a condenser lens, a dichroic mirror, a band-pass filter and the like that focus and irradiate laser light on cells, and a detection system that detects measurement target light generated from the cells due to the irradiation of the LD. The detection system is configured from, for example, a PMT (photo multiplier tube), an area image sensor, such as a CCD or a CMOS element, and the like.

The measurement target light detected by the detection system in the light irradiation detection unit is light that is generated from the cells due to irradiation of measurement light. For example, this light may be scattered light, such as forward scattered light or side scattered light, Rayleigh scattered light, and Mie scattering, or fluorescence and the like. Such measurement target light is converted into an electric signal, output to the control unit, and used to determine the optical properties of the cells.

It is noted that the flow cytometer 1 may detect the properties of the cells either magnetically or electrically. In this case, microelectrodes are arranged facing the sample flow channel 22 of the microchip 2, and a resistance value, a capacitance value, an inductance value, impedance, changes in the electric field between the electrodes, or alternatively the magnetization and changes in the magnetic field and the like are measured.

2. Operation of the Microparticle Measurement Apparatus

Next, a method for analyzing microparticles (microparticle analysis method) with the microparticle measurement apparatus 1 according to an embodiment of the present technology will be described.

The microparticle measurement apparatus 1 according to an embodiment of the present technology irradiates the excitation light L1 on the droplet D by emitting the excitation light L1 from the first light source (LD) 3 toward the droplet D that is discharged from the orifice 21 of the microchip 2. At this point, fluorescence F and scattered light are emitted from the microparticles in the droplet D irradiated by the excitation light L1.

On the other hand, to acquire an image of the droplet D discharged from the orifice 21, the microparticle measurement apparatus 1 irradiates illumination light L2 on the droplet D by emitting the illumination light L2 from the second light source (LED) 4 toward the droplet D (refer to FIG. 1).

Further, the microparticle measurement apparatus 1 according to an embodiment of the present technology detects the fluorescence F emitted from the microparticles and acquires an image of the droplet D discharged from the orifice 21 with one light receiving element 5.

Since the signal intensity of the fluorescence F and the like emitted from the microparticles and the like is very small, detection is performed while ensuring a sufficient fluorescence intensity in order to perform an accurate detection.

Further, it is desirable to acquire a droplet image having a deep depth of field so as to efficiently confirm the formation state of the droplet D and detect changes in the position of the fluid stream S.

Accordingly, the microparticle measurement apparatus 1 according to an embodiment of the present technology is used by arranging the filter member 6, which has the first area 61 through which the illumination light L2 and the fluorescence F pass through and the second area 62 through which the fluorescence F passes but the illumination light L2 is blocked, between the droplet D and the light receiving element 5. The filter member 6 having the through hole 61 and the peripheral portion 62 is as described above.

In the microparticle measurement apparatus 1, the light receiving element 5 detects the fluorescence F that has passed through the first area 61 and the second area 62 of the filter member 6. At this time, the fluorescence F is acquired at a high NA without being blocked by the filter member 6 (refer to FIG. 3). Consequently, a sufficient fluorescence intensity can be ensured.

Further, a droplet image is acquired by the light receiving element 5 from the illumination light L2 that has passed through only the first area 61 of the filter member 6. The illumination light L2 is blocked by the second area 62 of the filter member 6, so that the droplet image is observed at a low NA (refer to FIG. 4). Consequently, the depth of field of the droplet image can be deeper.

Thus, as described above, with the flow cytometer 1, by using the above-described filter member 6 arranged between the droplet D and the light receiving element 5, the light receiving element 5 can detect the fluorescence generated from the microparticles in the droplets with hardly any decrease in signal intensity, and can acquire a droplet image with a deep depth of field.

Consequently, compared with a conventional droplet (or fluid stream) image, which has a shallow depth of field and is blurry, the flow cytometer 1 can eliminate the need for focus adjustment that has been manually performed with a focus adjustment mechanism, and can perform measurement and analysis simply and accurately. Further, since a focus adjustment mechanism is not necessary, the apparatus size is more compact, and costs can be reduced.

It should be understood by those skilled in the art that various modifications, combinations, sub-combinations and alterations may occur depending on design requirements and other factors insofar as they are within the scope of the appended claims or the equivalents thereof.

Additionally, the present technology may also be configured as below.

(1) A microparticle measurement apparatus including:
a first light source configured to irradiate excitation light on a droplet containing a microparticle, the droplet being discharged from an orifice;
a second light source configured to irradiate illumination light on the droplet for acquiring an image of the droplet;
a light receiving element configured to detect fluorescence generated from the microparticle due to the irradiation of the excitation light, and to acquire an image of the droplet; and
a filter member configured to be arranged between the droplet and the light receiving element,
wherein the filter member includes a first area through which the fluorescence and the illumination light pass, and a second area that is provided around the first area and that has a wavelength selectivity which lets the fluorescence pass through but blocks the illumination light.

(2) The microparticle measurement apparatus according to (1), wherein the first area is provided at a center portion of the filter member, and the second area is provided at a peripheral portion of the filter member.

(3) The microparticle measurement apparatus according to (1) or (2), wherein the first area is a through hole provided in the filter member.

(4) The microparticle measurement apparatus according to (1) or (2), wherein the first area is formed from a transparent member.

(5) The microparticle measurement apparatus according to any one of (1) to (4), wherein the second area is formed from a short-pass filter.

(6) The microparticle measurement apparatus according to any one of (1) to (5), wherein the second light source emits the illumination light having a longer wavelength than the fluorescence.

(7) The microparticle measurement apparatus according to any one of (1) to (6), wherein the second light source is an LED.

(8) A microparticle analysis method including:
irradiating excitation light on a droplet containing a microparticle and detecting, with a light receiving element, fluorescence generated from the droplet irradiated with the excitation light that has passed through a first area and a second area of a filter member, the droplet being discharged from an orifice; and
irradiating illumination light on the droplet and acquiring a droplet image with the light receiving element by blocking the illumination light irradiated on the droplet at the second area of the filter member and letting the illumination light pass through only the first area.

The present disclosure contains subject matter related to that disclosed in Japanese Priority Patent Application JP 2012-159754 filed in the Japan Patent Office on Jul. 18, 2012, the entire content of which is hereby incorporated by reference.

What is claimed is:
1. A microparticle measurement apparatus comprising:
a first light source configured to irradiate excitation light on a droplet containing a microparticle, the droplet being discharged from an orifice;
a second light source configured to irradiate illumination light on the droplet for acquiring an image of the droplet;
a light receiving element configured to detect fluorescence generated from the microparticle due to the irradiation of the excitation light, and to acquire an image of the droplet; and
a filter member configured to be arranged between the droplet and the light receiving element,
wherein the filter member includes a first area through which the fluorescence and the illumination light pass, and a second area that is provided around the first area and that has a wavelength selectivity which lets the fluorescence pass through but blocks the illumination light.

2. The microparticle measurement apparatus according to claim 1, wherein the first area is provided at a center portion of the filter member, and the second area is provided at a peripheral portion of the filter member.

3. The microparticle measurement apparatus according to claim 2, wherein the first area is a through hole provided in the filter member.

4. The microparticle measurement apparatus according to claim 2, wherein the first area is formed from a transparent member.

5. The microparticle measurement apparatus according to claim 3, wherein the second area is formed from a short-pass filter.

6. The microparticle measurement apparatus according to claim 5, wherein the second light source emits the illumination light having a longer wavelength than the fluorescence.

7. The microparticle measurement apparatus according to claim 6, wherein the second light source is an LED.

8. A microparticle analysis method comprising:
   irradiating excitation light on a droplet containing a microparticle and detecting, with a light receiving element, fluorescence generated from the droplet irradiated with the excitation light that has passed through a first area and a second area of a filter member, the droplet being discharged from an orifice; and
   irradiating illumination light on the droplet and acquiring a droplet image with the light receiving element by blocking the illumination light irradiated on the droplet at the second area of the filter member and letting the illumination light pass through only the first area.

* * * * *